United States Patent
Stasch et al.

(12) 
(10) Patent No.: US 6,693,102 B2
(45) Date of Patent: Feb. 17, 2004

(54) PYRIDINE-SUBSTITUTED PYRAZOLOPYRIDINE DERIVATIVES

(75) Inventors: Johannes-Peter Stasch, Soligen (DE); Achim Feurer, Odenthal (DE); Stefan Weigand, Wuppertal (DE); Elke Stahl, Bergisch Gladbach (DE); Dietmar Flubacher, Breisach (DE); Cristina Alonso-Alija, Haan (DE); Frank Wunder, Wuppertal (DE); Dieter Lang, Velbert (DE); Klaus Dembowsky, Boston, MA (US); Alexander Straub, Wuppertal (DE); Elisabeth Perzborn, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 1 day.

(21) Appl. No.: 10/001,569

(22) Filed: Nov. 1, 2001

(65) Prior Publication Data

US 2002/0173514 A1 Nov. 21, 2002

(30) Foreign Application Priority Data

Nov. 22, 2000 (DE) .......................................... 100 57 753
Jul. 2, 2001 (DE) .......................................... 101 31 987

(51) Int. Cl.[7] ...................... C07D 471/04; A61K 31/415
(52) U.S. Cl. ....................................... 514/256; 544/328
(58) Field of Search ........................... 544/328; 514/256

(56) References Cited

FOREIGN PATENT DOCUMENTS

| DE | 19920352 | 11/2000 |
|----|----------|---------|
| DE | 10021069 | 10/2001 |
| WO | 9816223  | 4/1998  |
| WO | 9816507  | 4/1998  |
| WO | 9823619  | 6/1998  |
| WO | 0006567  | 2/2000  |
| WO | 0006568  | 2/2000  |
| WO | 0006569  | 2/2000  |
| WO | 0021954  | 4/2000  |

OTHER PUBLICATIONS

Damasio, Alzheimer's Disease And Related Dementias, Cecil Textbook of Medicine, 20th Edition, vol. 2, pp. 1992–1996, 1996.*

Layzer, Degenerative Diseases of the Nervous System, Cecil Textbook of Medicine, 20th Edition, vol. 2, pp. 2050–2057, 1996.*

Glass, D. B., Frey II, W., Carr, D. W., Goldberg, N. D., "Stimulation of Human Platelet Cuanylate Cyclase by Fatty Acids", J. Biol. Chem., 252(4): 1279–1285 (Feb. 1977).

Ko, F.–N., Wu, C.–C., Kuo, S.–C., Lee, F.–Y., Teng, C.–M., "YC–1, a Novel Activator of Platelet Guanylate Cyclase", Blood, 84(12): 4226–4233 (Dec. 1994).

Mulsch, A., Bauersachs, J., Schafer, A., Stasch, J.–P., Kast, R., Busse, R., "Effect of YC–1, an NO–independent, superoxide–sensitive Stimulator of Soluble Guanylyl Cyclase, on Smooth Muscle Responsiveness to Nitrovasodilators", British Journal of Pharmacology, 120: 681–689 (1997).

Pettibone, D. J., Sweet, C. S., Risley, E. A., Kennedy, T., "A Structurally Novel Stimulator of Guanylate Cyclase with Long–Lasting Hypotensive Activity in the Dog", European Journal of Pharmacology, 116: 307–312 (1985).

Yu, S.–M., Kuo, S.–C., "Vasorelaxant Effect of Isoliquiritigenin, a Novel Soluble Guanylate Cyclase Activator, in Rat Aorta", British Journal of Pharmacology, 114: 1587–1594 (1995).

Straub. A., Stasch, J., Alonso–Alija, C., Benet–Buchholz, J., Ducke, B., Feurer, A., Furstner, C., "NO–Independent Stimulators of Soluble Guanylate Cyclase", Bioorganic & Medicinal Chemistry Letters, 11: 781–784 (2001).

* cited by examiner

*Primary Examiner*—Deepak Rao

(57) ABSTRACT

The present invention relates to new pyrazolopyridine derivatives of the formula (I)

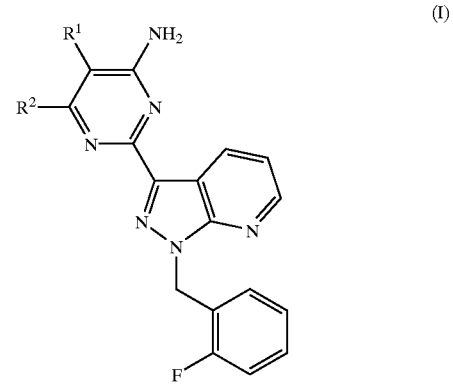

in which $R^1$ represents 4-pyridinyl or 3-pyridinyl; $R^2$ represents H, $NH_2$ or halogen; and salts, isomers and hydrates thereof as stimulators of soluble guanylate cyclase and for use as agents for the treatment of cardiovascular disorders, hypertension, of thromboembolic disorders and ischaemia, sexual dysfunction or inflammation, and for the treatment of disorders of the central nervous system.

15 Claims, No Drawings

PYRIDINE-SUBSTITUTED PYRAZOLOPYRIDINE DERIVATIVES

The present invention relates to new chemical compounds which stimulate soluble guanylate cyclase, their preparation and their use as medicaments, in particular as medicaments for the treatment of cardiovascular diseases.

One of the most important cellular transmission systems in mammals is cyclic guanosine monophosphate (cGMP). Together with nitrogen monoxide (NO) which is released from the endothelium and transmits hormonal and mechanical signals, it forms the NO/cGMP system. The guanylate cyclases catalyse the biosynthesis of cGMP from guanosine triphosphate (GTP). The representatives of this family known hitherto can be divided into two groups according to structural features and according to the nature of the ligands: the particulate guanylate cyclases, which can be stimulated by natriuretic peptides, and the soluble guanylate cyclases, which can be stimulated by NO. The soluble guanylate cyclases consist of two subunits and very highly probably contain one haem per heterodimer, which is a part of the regulatory centre. This has a central importance for the activation mechanism. NO can bind to the iron atom of the haem and thus markedly increase the activity of the enzyme. Haem-free preparations on the other hand, cannot be stimulated by NO. CO is also able to attack at the central iron atom of the haem, where the stimulation by CO is markedly lower than that by NO.

Owing to the formation of cGMP and the regulation of phosphodiesterases, iron channels and protein kinases resulting therefrom, guanylate cyclase plays a crucial role in different physiological processes, in particular in the relaxation and proliferation of smooth muscle cells, platelet aggregation and adhesion and neuronal signal transmission, and in diseases which are based on a disturbance of the abovementioned processes. Under pathophysiological conditions, the NO/cGMP system may be suppressed, which can lead, for example, to high blood pressure, platelet activation, increased cell proliferation, endothelial dysfunction, atherosclerosis, angina pectoris, cardiac insufficiency, thromboses, stroke and myocardial infarct.

An NO-independent possibility of treatment for diseases of this type, which is targeted at influencing the cGMP signal pathway in organisms, is a promising approach on account of the high efficiency and low side effects which are to be expected.

For therapeutic stimulation of the soluble guanylate cyclase, hitherto exclusively compounds such as organic nitrates have been used, whose action is based on NO. This is formed by bioconversion and activates the soluble guanylate cyclase by attacks on the central iron atom of the haem. Besides the side effects, the crucial disadvantages of this manner of treatment includes the development of tolerance.

In recent years, a few substances have been described which stimulate soluble guanylate cyclase directly, i.e. without prior release of NO, for example 3-(5'-hydroxymethyl-2'-furyl)-1-benzylindazole (YC-1, Wu et al., Blood 84 (1994), 4226; Mülsch et al., Br. J. Pharmacol. 120 (1997), 681), Fatty acids (Goldberg et al., J. Biol. Chem. 252 (1977), 1279), diphenyliodonium-hexafluorophosphate (Pettibone et al., Eur. J. Pharmacol. 116 (1985), 307), isoliquiritigenin (Yu et al., Brit. J. Pharmacol. 114 (1995), 1587) and various substituted pyrazole derivatives (WO 98/16223).

Furthermore, pyrazolopyridine derivatives have been described as stimulators of soluble guanylate cyclase in WO 98/16507, WO 98/23619, WO 00/06567, WO 00/06568, WO 00/06569 and WO 00/21954. In these patent applications, pyrazolopyridines are also described which have a pyrimidine radical in the 3 position. Compounds of this type have a very high in vitro activity with respect to the stimulation of soluble guanylate cyclase. However, it has been seen that these compounds have some disadvantages with respect to their in vivo properties, for example their behaviour in the liver, their pharmacological behaviour, their dose-response relationship or their metabolization pathway.

It was therefore the object of the present invention to provide further pyrazolopyridine derivatives which act as stimulators of soluble guanylate cyclase, but which do not have the abovementioned disadvantages of the compounds from the prior art.

This object is achieved according to the present invention by the compounds according to claim 1. These new pyrazolopyridine derivatives are distinguished by a pyrimidine radical in the 3 position which has a certain substitution pattern, namely a pyridine radical in the 5 position of the pyrimidine ring and an amino group in the 4 position of the pyrimidine ring.

Specifically, the present invention relates to the compounds of the formula (I)

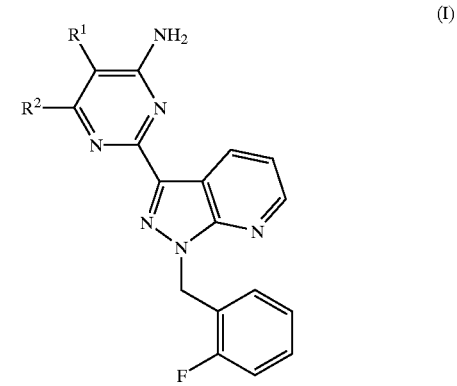

in which
R$^1$ represents 4-pyridinyl or 3-pyridinyl;
R$^2$ represents H, NH$_2$ or halogen;
and salts, isomers and hydrates thereof.

According to an alternative embodiment the present invention relates to the compounds of the formula (I), wherein
R$^1$ represents 4-pyridinyl or 3-pyridinyl;
R$^2$ represents H, NH$_2$ or Cl;
and salts, isomers and hydrates thereof.

According to a further alternative embodiment the present invention relates to the compounds of the formula (I), wherein
R$^1$ represents 4-pyridinyl or 3-pyridinyl;
R$^2$ represents H;
and salts, isomers and hydrates thereof.

The compounds of the formula (I) according to the invention can also be present in the form of their salts. In general, salts with organic or inorganic bases or acids may be mentioned here.

In the context of the present invention, physiologically acceptable salts are preferred. Physiologically acceptable salts of the compounds according to the invention can be salts of the substances according to the invention with mineral acids, carboxylic acids or sulphonic acids. Particularly preferred salts, for example, are those with hydrochloric acid, hydrobromic acid, sulphuric acid, phosphoric acid, methanesulphonic acid, ethanesulphonic acid, p-toluenesulphonic acid, benzenesulphonic acid, naphthalenedisulphonic acid, acetic acid, propionic acid, lactic acid, tartaric acid, citric acid, fumaric acid, maleic acid or benzoic acid.

Physiologically acceptable salts can likewise be metal or ammonium salts of the compounds according to the invention which have a free carboxyl group. Those particularly preferred are, for example, sodium, potassium, magnesium or calcium salts, and also ammonium salts which are derived from ammonia, or organic amines such as ethylamine, di- or triethylamine, di- or triethanolamine, dicyclohexylamine, dimethylaminoethanol, arginine, lysine or ethylenediamine.

The compounds according to the invention can be present in tautomeric forms. This is known to the person skilled in the art, and forms of this type are likewise included by the scope of the invention.

The compounds according to the invention can furthermore occur in the form of their possible hydrates.

Halogen in the context of the present invention represents fluorine, chlorine, bromine and iodine.

The compounds of the formula (I) according to the invention can be prepared by the reaction of the compound of the formula (II)

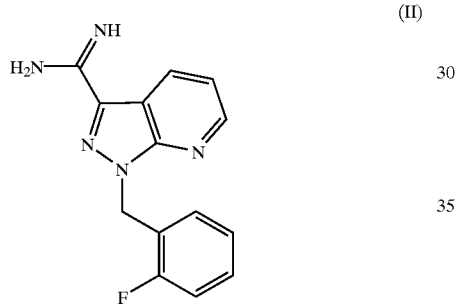

(II)

A) with a compound of the formula (III)

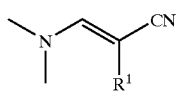

(III)

where
$R^1$ is as defined above;
if appropriate in an organic solvent, with heating to give the compound of the formula (I);
or
B) with a compound of the formula (IV)

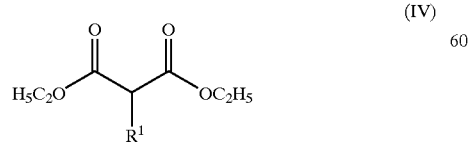

(IV)

where
$R^1$ is as defined above;

in an organic solvent under heating to compounds of the formula (V)

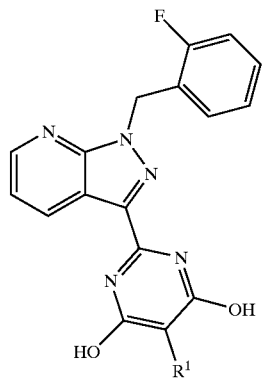

(V)

where
$R^1$ is as defined above;
subsequently with a halogenating agent to compounds of the formula (VI)

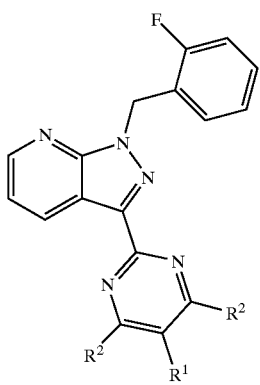

(VI)

where
$R^1$ is as defined above;
$R^2$ represent halogen;
and finally with aqueous ammonia solution under heating and elevated pressure.

The compound of the formula (II) can be prepared according to the following reaction scheme:

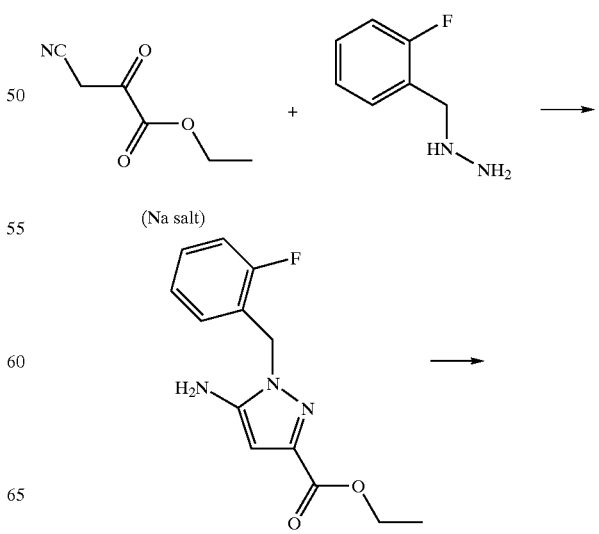

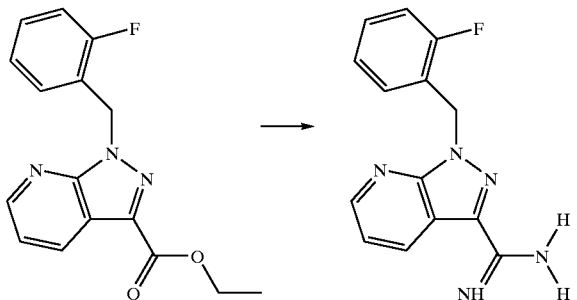

The compound of the formula (II) is obtainable in a multi-stage synthesis from the sodium salts of ethyl cyanopyruvate, which is known from the literature (Borsche and Manteuffel, Liebigs. Ann. Chem. 1934, 512, 97). By reaction thereof with 2-fluorobenzylhydrazine with heating and under a protective gas atmosphere in an inert solvent such as dioxane, ethyl 5-amino-1-(2-fluorobenzyl)pyrazole-3-carboxylate is obtained, which cyclizes by means of reaction with dimethylaminoacrolein in the acidic medium under a protective gas atmosphere and with heating to give the corresponding pyridine derivative. This pyridine derivative, ethyl 1-(2-fluorobenzyl)-1H-pyrazolo[3,4-b]pyridine-3-carboxylate, is converted by means of a multi-stage sequence, consisting of conversion of the ester into the corresponding amide using ammonia, dehydration using a dehydrating agent such as trifluoroacetic anhydride to give the corresponding nitrite derivative, reaction of the nitrile derivative with sodium ethoxide and final reaction with ammonium chloride, into the compound of the formula (II).

The compounds of the formula (III) can be prepared from the compounds t-butoxybis(dimethylamino)methane and 4-pyridylacetonitrile or 3-pyridylacetonitrile, which are commercially obtainable (e.g. from Aldrich), by reaction of these reactants, preferably in equimolar amounts, preferably at normal pressure and with stirring of the reaction solution for a number of hours, for example 2 hours, at elevated temperature, for example 60–130° C., preferably 80–120° C., in particular 100° C.

The reaction of the compounds of the formulae (II) and (III) to give the compounds of the formula (I) can be carried out by use of the reactants in equimolar amounts or using the compound of the formula (III) in a slight excess in an organic solvent, for example a hydrocarbon, preferably an aromatic hydrocarbon and in particular xylene, preferably in the presence of 0.1–1 equivalent, preferably 0.3 equivalent, of a Lewis acid such as $BF_3Et_2O$ or trimethylsilyl trifluorosulphonate (TMSOTf), preferably at normal pressure and with stirring of the reaction solution for a number of hours, for example 12 hours, at elevated temperature, for example 80–160° C., preferably 100–150° C., in particular 140° C.

The compounds of the formula (IV) are commercially obtainable (e.g. from Mercachem) or can be synthesized by methods known to the man skilled in the art.

The conversion of the compounds of formulae (II) and (IV) to the compounds of the formula (V) can be carried out using either equimolar amounts of the reactants or a slight excess of the compound of formula (IV) in an organic solvent, for example a hydrocarbon, preferably an aromatic hydrocarbon and especially toluene, preferably under normal pressure and stirring of the reaction solution for several hours, for example 12 hours, under elevated temperature, for example 80–160° C., especially 140° C.

The conversion of the compounds of formula (V) to the compounds of formula (VI) can be carried outby reacting the compounds of formula (V) with a halogenating agent, optionally in an organic solvent conventionally used for such reactions, for example in dimethylformamide (DMF), preferably under normal pressure and stirring of the reaction solution for several hours, for example 3 hours, under elevated temperature, for example 80–160° C., especially 120° C. According to the invention the use of $POCl_3$ as halogenating agent is preferred.

The conversion of the compounds of the formula (VI) to the compounds of the invention according to formula (I) can be carried out by reacting the compounds of the formula (VI) with aqueous ammonia solution preferably under elevated pressure, for example by carring out the reaction in an autoclave letting the reaction proceed under the pressure of the reaction solution itself, and stirring of the reaction solution for several hours, for example 12 hours, under elevated temperature, for example 80–160° C., preferably 100–150° C., especially 140° C.

The compounds of the formula (I) according to the invention show an unforeseeable, valuable spectrum of pharmacological activity.

The compounds of the formula (I) lead to vasorelaxation, inhibition of platelet aggregation and to a lowering of blood pressure and to an increase in the coronary blood flow. These actions are mediated via direct stimulation of soluble guanylate cyclase and an intracellular cGMP increase. Moreover, the compound of the formula (I) according to the invention potentiates the action of substances which increase the cGMP level, for example EDRF (endothelium-derived relaxing factor), NO donors, protoporphyrin IX, arachidonic acid or phenylhydrazine derivatives.

They can therefore be employed in medicaments for the treatment of cardiovascular diseases, for example for the treatment of high blood pressure and cardiac insufficiency, stable and unstable angina pectoris, peripheral and cardiac vascular diseases, of arrthythmias, for the treatment of thromboembolic diseases and ischaemias such as myocardial infarct, stroke, transitory and ischaemic attacks, peripheral circulatory disorders, prevention of restenoses such as after thrombosis therapy, percutaneous transluminal angioplasty (PTA), percutaneous transluminal coronary angioplasty (PTCA), bypass and also for the treatment of arteriosclerosis, asthmatic conditions and diseases of the urogenital system such as prostate hypertrophy, erectile dysfunction, female sexual dysfunction, osteoporosis, gastroparesis and incontinence.

The compounds of the formula (I) described in the present invention are also active compounds for the control of diseases in the central nervous system which are characterized by disturbances of the NO/cGMP system. In particular, they are suitable for improving the perception, concentration powder, learning power or memory power after cognitive disorders, such as occur, in particular, in situations/diseases/syndromes such as mild cognitive impairment, age-associated learning and memory disorders, age-associated memory losses, vascular dementia, craniocerebral trauma, stroke, dementia which occurs after strokes (post-stroke dementia), post-traumatic craniocerebral trauma, general concentration disorders, concentration disorders in children with learning and memory problems, Alzheimer's disease, vascular dementia, dementia with Lewy bodies, dementia with degeneration of the frontal lobes including Pick's dementia, Parkinson's disease, progressive nuclear palsy, dementia with corticobasal degeneration, amyolateral sclerosis (ALS), Huntington's disease, multiple sclerosis, thalamic degeneration, Creutzfeld-Jacob dementia, HIV dementia, schizophrenia with dementia or Korsakoff psychosis. They are also suitable for the treatment of disorders of the central nervous system such as states of anxiety, tension and depression, central nervous system-related sexual dysfunctions and sleep disorders, and for the regulation of pathological disorders of the absorption of food, tea, coffee, etc. and addictive drugs.

Furthermore, the active compounds are also suitable for regulating the cerebral circulation and are thus effective agents for the control of migraine.

They are also suitable for the prophylaxis and control of the sequellae of cerebral infarcts (cerebral apoplexy), such as stroke, cerebral ischaemias and craniocerebral trauma. The compounds of the formula (I) according to the invention can likewise be employed for the control of painful conditions.

The compounds according to the invention moreover have anti-inflammatory action and can therefore be employed as anti-inflammatory agents.

The invention moreover includes the combination of the compounds of the formula (I) according to the invention with organic nitrates and NO donors.

Organic nitrates and NO donors in the context of the invention are generally substances which display their therapeutic action via the release of NO or NO species. Sodium nitroprusside, nitroglycerin, isosorbide dinitrate, isosorbide mononitrate, molsidomine and SIN-1 are preferred.

The invention moreover includes the combination with compounds which inhibit the breakdown of cyclic guanosine monophosphate (cGMP). These are, in particular, inhibitors of phosphodiesterases 1, 2 and 5; nomenclature according to Beavo and Reifsynder (1990) TiPS 11 pp. 150 to 155. By means of these inhibitors, the action of the compounds according to the invention is potentiated and the desired pharmacological effect is increased.

Biological Investigations
Vasorelaxant Action in Vitro

Rabbits are stunned by a blow to the neck and exsanguinated. The aorta is removed, freed from adherent tissue, divided into rings 1.5 mm wide and individually transferred under a pretension to 5 ml organ baths containing carbogen-aerated Krebs-Henseleit solution of the following composition (mM) at 37° C.: NaCl: 119; KCl: 4.8; $CaCl_2 \times 2H_2O$: 1; $MgSO_4 \times 7H_2O$; 1.4; $KH_2PO_4$: 1.2; $NaHCO_3$:25; Glucose: 10. The contractile force is determined using Statham UC2 cells, amplified and digitalized by means of A/D converters (DAS-1802 HC, Keithley Instruments Munich), and recorded in parallel on linear recorders. To produce a contraction, phenylephrine is added to the bath cumulatively in increasing concentration. After several control cycles, the substance to be investigated is investigated in each further passage in increasing dose in each case and the height of the contraction is compared with the height of the contraction reached in the last previous passage. From this, the concentration is calculated which is necessary in order to reduce the height of the control value by 50% ($IC_{50}$). The standard administration volume is 5 µl and the proportion of DMSO in the bath solution corresponds to 0.1%. The result is shown below in Table 1:

TABLE 1

Vasorelaxant action in vitro

| Example No. | $IC_{50}$ [µM] |
|---|---|
| 1 | 0.66 |
| 4 | 1.21 |

Determination of the Liver Clearance in Vitro

Rats are anesthetized, heparinized, and the liver is profused in situ via the portal artery. Ex vivo, the primary rat hepatocytes are then obtained from the liver by means of collagenase solution. $2 \cdot 10^6$ hepatocytes per ml were incubated at 37° C. with the same concentration in each case of the compound to be investigated. The decrease of the substrate to be investigated over time was determined bioanalytically (HPLC/UV, HPLC/fluorescence or LC/MSMS) at 5 points in time in each case in the period from 0–15 min after the start of incubation. From this, the clearance was calculated by means of the cell count and liver weight.

Determination of the Plasma Clearance in Vivo

The substance to be investigated is administered intravenously to rats via the tail vein as a solution. At fixed points in time, blood is taken from the rats, heparinized and plasma is obtained therefrom by conventional measures. The substance is quantified bioanalytically in the plasma. The pharmacokinetic parameters are calculated from the plasma concentration-time courses determined in this way by means of conventional non-compartmental methods used for this purpose.

The present invention includes pharmaceutical preparations which, in addition to non-toxic, inert pharmaceutically suitable vehicles, contain the compounds of the formula (I) according to the invention, and processes for the production of these preparations.

The active compound can optionally also be present in microencapsulated form in one or more of the vehicles indicated above.

The therapeutic reactive compound of the formula (I) should be present in the abovementioned pharmaceutical preparations in a concentration of approximately 0.1 to 99.5% by weight, preferably of approximately 0.5 to 95% by weight, of the total mixture.

Apart from the compounds of the formula (I) according to the invention, the abovementioned pharmaceutical preparations can also contain further pharmaceutical active compounds.

In general, it has proven advantageous both in human and in veterinary medicine to administer the active compound according to the invention in total amounts of approximately 0.01 to approximately 700, preferably 0.01 to 100, mg/kg of body weight every 24 hours, if appropriate in the form of several individual doses, to achieve the desired results. An individual dose contains the active compound according to the invention preferably in amounts from approximately 0.1 to approximately 80, in particular 0.1 to 30, mg/kg of body weight.

The present invention is shown below in greater detail with the aid of non-restricting preferred examples. If not stated otherwise, all quantitative data relate to percentages by weight.

EXAMPLES

| Abbreviations: | |
|---|---|
| RT: | room temperature |
| EA: | ethyl acetate |
| MCPBA: | m-chloroperoxybenzoic acid |
| BABA: | n-butyl acetate/n-butanol/glacial acetic acid/phosphate buffer pH 6 (50:9:25.15; org. phase) |
| DMF: | N,N-dimethylformamide |

-continued

Eluent for thin-layer chromatography:

| T1 E1: | toluene - ethyl acetate (1:1) |
| T1 EtOH1: | toluene - methanol (1:1) |
| C1 E1: | cyclohexane - ethyl acetate (1:1) |
| C1 E2: | cyclohexane - ethyl acetate (1:2) |

Methods for the Determination of HPLC—Retention Times or Preparative Methods of Separation method A=(LC–MS):

eluent:
A=acetonitrile+0.1% formic acid,
B=water+0.1% formic acid flow: 25 ml/min temperature: 40° C.

packaging material: Symmetry C 18, 50×2.1 mm, 3.5 μm.

| time (min) | A | B |
|---|---|---|
| 0 | 10 | 90 |
| 4.0 | 90 | 10 |
| 6.0 | 90 | 10 |
| 6.1 | 10 | 90 |
| 7.5 | 10 | 90 | method B (preparative HPLC):

eluent:
A=Milli-Q-water+0.6 g concentrated hydrochloric acid with 11 H$_2$O
B=acetonitrile flow: 50 ml/min temperature: room temperature packaging material: YMC-Gel ODS-AQS 11 μm 250×30 mm

| time (min) | A | B |
|---|---|---|
| 0 | 90 | 10 |
| 3 | 90 | 10 |
| 27 | 2 | 98 |
| 34 | 2 | 98 |
| 34.01 | 90 | 10 |
| 38 | 90 | 10 |

Starting Compounds

I. Synthesis of 4-[(dimethylamino)methylene]-pyridineacetonitrile (E/Z mixture)

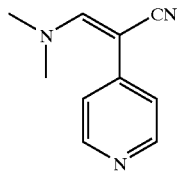

7.52 g (63.7 mmol) of 4-pyridylacetonitrile and 11.09 g (63.7 mmol) of tert-butoxybis(dimethylamino)methane were stirred at 100° C. for 2 h. In the course of this, liberated dimethylamine and t-butanol were led off to the atmosphere by a slight reduced pressure flow by means of a vacuum pump. Flash chromatography (CH$_2$Cl$_2$/ethyl acetate 50:1→20:1) yielded the title compound.

Yield: 10.2 g (93%)

R$_f$: 0.29 (CH$_2$Cl$_2$/EA 20/1)

$^1$H-NMR: (300 MHz, D$_6$-DMSO), δ=3.25 (s, 6 H, 2×CH$_3$), 7.25 (d, 2 H, Ar—H), 7.80 (s, 1 H, Ar—H), 8.33 (d, 2 H, Ar—H).

MS: (ESI pos.), m/z=174 ([M+H]$^+$)

II. Synthesis of 3-[(dimethylamino)methylene]-pyridineacetonitrile (E/Z mixture)

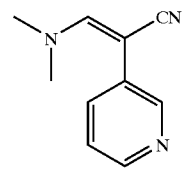

3.00 g (25.4 mmol) of 3-pyridylacetonitrile and 4.23 g (25.4 mmol) tert-butoxybis(dimethylamino)methane were stirred at 100° C. for 2 h. In the course of this, liberated dimethylamine and t-butanol were led off to the atmosphere by a slight reduced pressure flow by means of a vacuum pump. After cooling, the deposited solid was filtered, washed with a little H$_2$O and the title compound was thus obtained.

Yield: 4.23 g (96%)

R$_f$: 0.27 (CH$_2$Cl$_2$/MeOH 40/1)

$^1$H-NMR: (300 MHz, D$_6$-DMSO), δ=3.08 (s, 3 H, CH$_3$), 3.25 (s, 3 H, CH$_3$), 7.29 (dd, 1 H, Ar—H), 7.57 (s, 1 H, =C—H), 7.66 (dt, 1 H, Ar—H), 8.26 (d, 1 H, Ar—H), 8.54 (d, 1 H, Ar—H).

LCMS: Ret. time: 0.33 min (column: Symmetry, C-18, 3.5 μm, 50×2.1 mm, flow 0.5 ml/min, 40° C., gradient: water (+0.1% formic acid): acetonitrile (+0.1% formic acid) at 0 min: 90:10, at 7.5 min 10:90)); MS: (ESI pos.), m/z=174 ([M+H]$^+$)

III. Synthesis of 1-(2-fluorobenzyl)1H-pyrazolo[3,4-b]pyridine-3-carboxamidine

3A) Ethyl 5-amino-1-(2-fluorobenzyl)-pyrazole-3-carboxylate

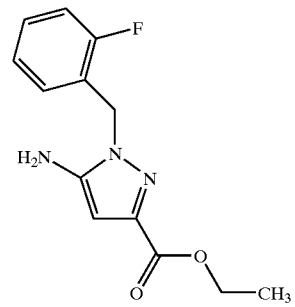

100 g (0.613 mol) of sodium salt of ethyl cyanopyruvate (preparation analogously to Borsche and Manteuffel, Liebigs Ann. 1934, 512, 97) are treated with 111.75 g (75 ml, 0.98 mol) of trifluoroacetic acid at room temperature in 2.5 l of dioxane under argon with good stirring and the mixture is stirred for 10 min, a large part of the starting material going into solution. 85.93 g (0.613 mol) of 2-fluorobenzylhydrazine are then added and the mixture is boiled overnight. After cooling, the deposited crystals of sodium trifluoroacetate are filtered off with suction, washed with dioxane and the solution is reacted further in crude form.

3B) Ethyl 1-(2-fluorobenzyl)-1H-pyrazolo[3,4-b]pyridine-3-carboxylate

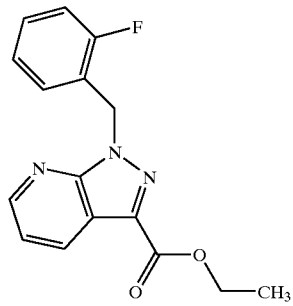

The solution obtained from 3A) is treated with 61.25 ml (60.77 g, 0.613 mol) of dimethylaminoacrolein and 56.28 ml (83.88 g, 0.736 mol) of trifluoroacetic acid and boiled under argon for 3 days. The solvent is then evaporated in vacuo, the residue is added to 2 l of water and the mixture is extracted three times with 1 l of ethyl acetate each time. The combined organic phases are dried using magnesium sulphate and concentrated in a rotary evaporator. The residue is chromatographed on 2.5 g of silica gel and eluted with a toluene/toluene-ethyl acetate=4:1 gradient. Yield: 91.6 g (49.9% of theory over two steps).

M.p. 85° C.

$R_f(SiO_2, T1E1)$: 0.83

3C) 1-(2-Fluorobenzyl)-1H-pyrazolo[3,4-b]pyridine-3-carboxamide

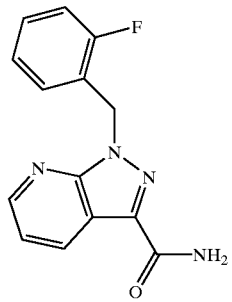

10.18 g (34 mmol) of the ester obtained in Example 3B) are introduced into 150 ml of methanol saturated with ammonia at 0–10° C. The mixture is stirred at room temperature for two days and then concentrated in vacuo. $R_f(SiO_2, T1E1)$: 0.33

3D) 3-Cyano-1-(2-fluorobenzyl)-1H-pyrazolo[3,4-b]pyridine

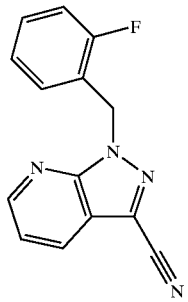

36.1 g (133 mmol) of 1-(2-fluorobenzyl)-1H-pyrazolo[3,4-b]pyridine-3-carboxamide from Example 3C) are dissolved in 330 ml of THF and treated with 27 g (341 mmol) of pyridine. 47.76 ml (71.66 g, 341 mmol) of trifluoroacetic anhydride are then added in the course of 10 min, the temperature rising to 40° C. The mixture is stirred overnight at room temperature. The batch is then added to 1 l of water and extracted three times with 0.5 l of ethyl acetate each time. The organic phase is washed with saturated sodium hydrogencarbonate solution and with 1 N HCl dried using $MgSO_4$ and concentrated in a rotary evaporator.

Yield: 33.7 g (100% of theory)

M.p: 81° C.

$R_f(SiO_2, T1E1)$: 0.74

3E) Methyl (2-fluorobenzyl)-1H-pyrazolo[3, 4-b]pyridine-3-carboximidate

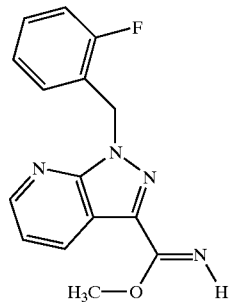

30.37 g (562 mmol) of sodium methoxide are dissolved in 1.5 l of methanol and 36.45 g (144.5 mmol) of 3-cyano-1-(2-fluorobenzyl)-1H-pyrazolo[3,4-b]pyridine (from Example 3D) are added. The mixture is stirred at room temperature for 2 hours and the solution obtained is employed directly for the next step.

3F) 1-(2-Fluorobenzyl)1H-pyrazolo[3, 4-b]pyridine-3-carboxamidine

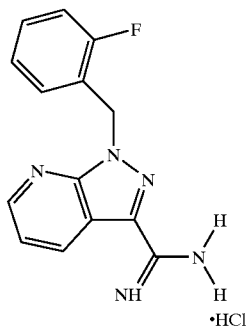

The solution of methyl (2-fluorobenzyl)-1H-pyrazolo[3,4-b]pyridine-3-carboximidate obtained from Example 3E) in methanol is treated with 33.76 g (32.19 ml, 562 mmol) of glacial acetic acid and 9.28 g (173 mmol) of ammonium chloride and stirred overnight under reflux. The solvent is evaporated in vacuo, the residue is triturated well with acetone and the deposited solid is filtered off with suction.

$^1$H-NMR (d$_6$-DMSO, 200 MHz): δ=5.93 (s, 2H); 7.1–7.5 (m, 4 H); 7.55 (dd, 1H); 8.12 (dd, 1H); 8.30 (dd, 1H); 9.5 (bs, 4H-exchangeable) ppm.

MS (EI): m/z=270.2 (M—HCl)

IV. Synthesis of 2-[1-(2-fluorobenzyl)-1H-pyrazolo[3,4-b]pyridine-3-yl]-5-(4-pyridinyl)-4,6-pyrimidinediol

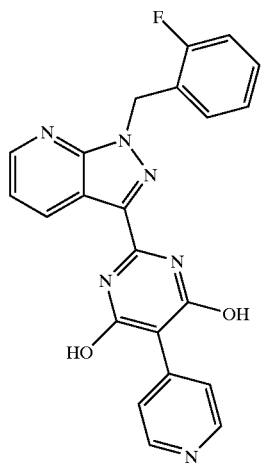

3.27 g (12.1 mmol) 1-(2-fluorobenzyl)-1H-pyrazolo[3,4-b]pyridine-3-carboximid-amide from example III were suspended in 40 ml toluene, reacted with 2.88 g (12.1 mmol) diethyl 2-(4-pyridinyl)malonate (commercially available by Mercachem) and stirred overnight at 140° C. For purification the deposited solid is sucked off and dried under high vacuum.

Yield: 2.43 g (43%)

LC-MS: R$_t$=2.69 min (method A). MS (ESI pos.), m/z= 415 ([M+H]$^+$).

V. Synthesis of 3-[4,6-dichloro-5-(4-pyridinyl)-2-pyrimidinyl]-1-(2-fluorobenzyl)-1H-pyrazolo-[3,4-b]pyridine

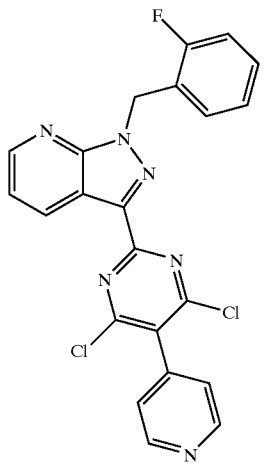

2.39 g (5.77 mmol) of 2-[1-(2-fluorobenzyl)-1H-pyrazolo[3,4-b]pyridine-3-yl]-5-(4-pyridinyl)-4,6-pyrimidinediol from example IV were dissolved in 10 ml phosphorylchloride. 3 drops of DMF were added thereto and it was stirred for 3 h under reflux. For purification the reaction solution was concentrated and dried under high vacuum.

Yield: 0.67 g (24%)

LC-MS: R$_t$=4.34 min (method A). MS (ESI pos.), m/z= 451 ([M+H]$^+$, Cl$_1$).

EXAMPLES 1. 2-[1-[(2-Fluorophenyl)methyl]-1H-pyrazolo[3,4-b]pyridin-3-yl]-5-(4-pyridinyl)-4-pyrimidinamine

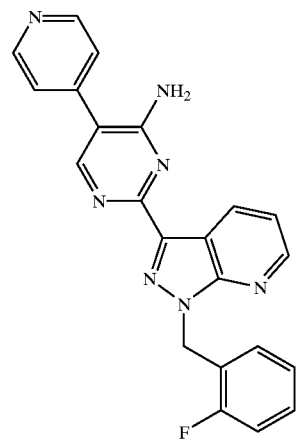

0.50 g (1.9 mmol) of 1-(2-fluorobenzyl)-1H-pyrazolo[3,4-b]pyridine-3-carboximid-amide from Ex. III and [(dimethylamino)methylene]-pyridineacetonitrile (0.32 g, 1.9 mmol) from Ex. I were suspended in xylene and treated with BF$_3$×OEt$_2$ (71 μl, 79 mg, 0.56 mmol, 0.3 equiv.). After 19 h at 140° C., the mixture was allowed to cool to room temperature and concentrated in vacuo. It was possible to purify the title compound by flash chromatography on silica gel (CH$_2$Cl$_2$:MeOH 20:1) and subsequent extraction by stirring in acetonitrile.

Yield: 0.24 g (33%)

R$_f$: 0.17 (EA/MeOH 20:1)

B.p: 254° C.

Retention time: 2.7 min (column: Symmetry, C-18, 3.5 μm, 50×2.1 mm, flow 0.5 ml/min, 40° C., gradient: wasser (+0.1% formic acid): acetonitrile (+0.1% formic acid) at 0 min: 90:10, at 7.5 min 10:90))

$^1$H-NMR: (300 MHz, D$_6$-DMSO), δ=5.81 (s, 2H, CH$_2$), 7.0–7.6 (m, 9 H, Ar—H, NH$_2$), 8.64 (m$_c$, 3 H, Ar—H), 9.05 (d, 1 H, Ar—H)

MS: (ESI pos.), m/z=398 ([M+H]$^+$), (ESI neg.), m/z=396 ([M–H]$^+$)

2. 2-[1-[(2-fluorophenyl)methyl]-1H-pyrazolo[3,4-b] pyridin-3-yl]-5-(4-pyridinyl)-4-pyrimidinamine

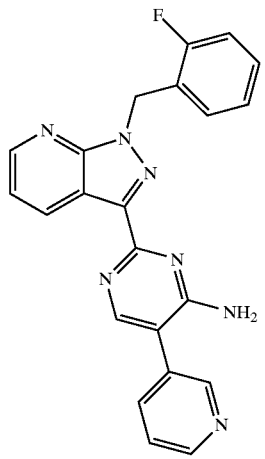

4.00 g (14.9 mmol) of 1-(2-fluorobenzyl)-1H-pyrazolo[3,4-b]pyridine-3-carboximid-amide from Ex. III and 3-[(dimethylamino)methylene]-pyridineacetonitrile (2.57 g, 14.9 mmol) from Ex. II were suspended in xylene. After 12 h at 120° C., the mixture was allowed to cool to room temperature and the deposited precipitate was filtered. The mother liquor was purified by preparative HPLC (column: Cromsil 120 ODS, C-18, 10 μm, 250×30 mm, flow 50 ml/min, room temperature, gradient: water acetonitrile at 0 min: 90:10, at 28 min 5:95). The purification process had to be repeated.

Yield: 0.024 g (0.4%)

R$_f$: 0.17 (EA/MeOH 20:1)

$^1$H-NMR: (200 MHz, D$_6$-DMSO), δ=5.81 (s, 2H, OCH$_2$), 6.95–7.6 (m, 8 H, Ar—H, NH$_2$), 7.92 (dt, 1 H, Ar—H), 8.21 (S, 1H, Ar—H), 8.6–8.75 (m, 2 H, Ar—H), 9.03 (dd, 1 H, Ar—H).

LCMS: Ret. time: 2.66 min (column: Symmetry, C-18, 3.5 μm, 50×2.1 mm, flow 0.5 ml/min, 40° C., gradient: water (+0.1% formic acid): aceto-nitrile (+0.1% formic acid) at 0 min: 90:10, at 7.5 min 10:90)); MS: (ESI pos.), m/z=398 ([M+H]$^+$), (ESI neg.), m/z=396 ([M–H]$^+$)

3. 6-chloro-2-[1-(2-fluorobenzyl)-1H-pyrazolo[3,4-b]pyridine-3-yl]-5-(4-pyridinyl)-4-pyrimidinylamine

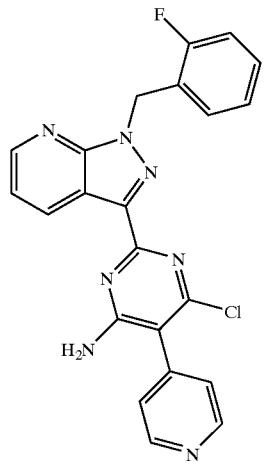

200 mg (0.443 mmol) of 3-[4,6-dichloro-5-(4-pyridinyl)-2-pyrimidinyl]-1-(2-fluorobenzyl)-1H-pyrazolo-[3,4-b] pyridine from example V were suspended in 5 ml 25% aqueous ammonia solution and stirred overnight in an autoclave at 140° C. under the pressure of the reaction solution itself. The mixture was extracted three times with dichloromethane, the combined extracts dried over magenisum sulfate and evaporated to dryness. The residue was purified by chromatography at silicagel with dichlormethane/methanol 30:1. For further purification the raw product was purified by preparative HPLC (method B).

Yield: 34 mg (15%)

R$_f$ 0.45 (CH$_2$Cl$_2$/MeOH 20:1)

$^1$H-NMR: (300 MHz, D$_6$-DMSO), δ=5.85 (s, 2H, CH$_2$), 7.10–7.48 (m, 9H, 7Ar—H and NH$_2$), 8.61–8.75 (m, 3H, Ar—H), 8.99 (dd, 1H, Ar—H).

LC-MS: R$_t$=3.55 min (method A). MS (ESI pos.), m/z= 432.3 ([M+H]$^+$), 885.2 ([2M+Na]$^+$).

4. 2-[1-(2-fluorobenzyl)-1H-pyrazolo[3,4-b] pyridine-3-yl]-5-(4-pyridinyl)-4,6-pyrimidine diamine

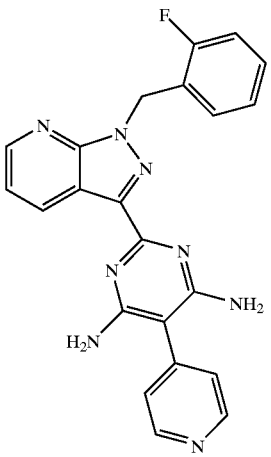

200 mg (0.443 mmol) of 3-[4,6-dichloro-5-(4-pyridinyl)-2-pyrimidinyl]-1-(2-fluorobenzyl)-1H-pyrazolo-[3,4-b]

pyridine from example V were suspended in 5 ml 25% aqueous ammonia solution and stirred overnight in an autoclave at 140° C. under the pressure of the reaction solution itself. The mixture was extracted three times with dichloromethane, the combined extracts dried over magenisum sulfate and evaporated to dryness. The residue was purified by chromatography at silicagel with dichlormethane/methanol 30:1. For further purification the raw product was purified by preparative HPLC (method B).

Yield: 45 mg (20%)

$R_f$ 0.30 ($CH_2Cl_2$/MeOH 20:1)

$^1$H-NMR: (300 MHz, $D_6$-DMSO), δ=5.82 (s, 2H, $CH_2$), 6.02 (br.s, 4H, $NH_2$), 7.08–7.48 (m, 7H, Ar—H), 8.57–8.68 (m, 3H, Ar—H), 9.13 (dd, 1H, Ar—H).

LC-MS: $R_t$=2.55 min (method A). MS (ESI pos.), m/z= 413.3 ($[M+H]^+$), 847.8 ($[2M+Na]^+$).

What is claimed is:
1. A compound of formula (I)

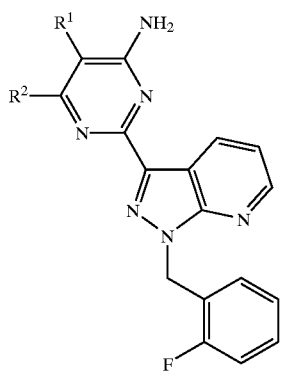

(I)

in which

R$^1$ represents 4-pyridinyl or 3-pyridinyl; and
R$^2$ represents H, NH$_2$ or halogen;

or a pharmaceutically acceptable salt, tautomer, or hydrate thereof.

2. The compound according to claim 1, in which

R$^1$ represents 4-pyridinyl or 3-pyridinyl; and
R$^2$ represents H, NH$_2$ or Cl;
  or a pharmaceutically acceptable salt, tautomer, or hydrate thereof.

3. The compound according to claim 1, in which

R$^1$ represents 4-pyridinyl or 3-pyridinyl; and
R$^2$ represents H;
  or a pharmaceutically acceptable salt, tautomer, or hydrate thereof.

4. The compound having the formula

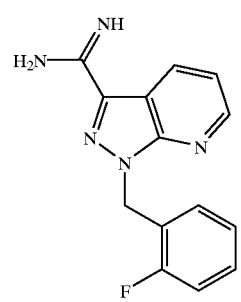

or a pharmaceutically acceptable salt, tautomer, or hydrate thereof.

5. A process for the preparation of compounds of formula (I), comprising reacting a compound of formula (II)

(II)

A) with a compound of formula (III)

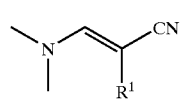

(III)

in which
  R$^1$ represents 4-pyridinyl or 3-pyridinyl;
  optionally in an organic solvent, with heating to give a compound of the formula (I);

or

B) with a compound of formula (IV)

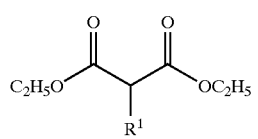

(IV)

in which
  R$^1$ represents 4-pyridinyl or 3-pyridinyl;
  in an organic solvent under heating to give a compound of formula (V)

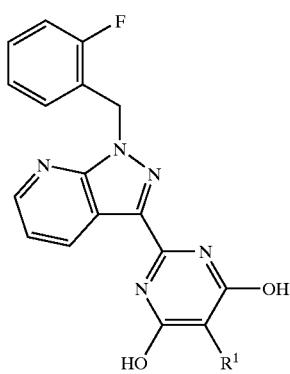

(V)

in which
R¹ represents 4-pyridinyl or 3-pyridinyl; and
subsequently reacting (V) with a halogenating agent to give a compound of formula (VI)

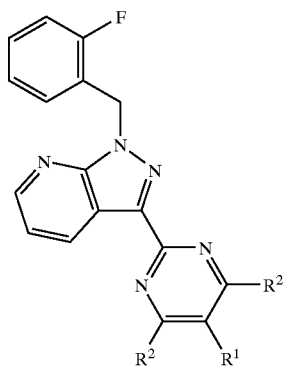

(VI)

in which
R¹ represents 4-pyridinyl or 3-pyridinyl; and
R² represent halogen;

and finally reacting (VI) with aqueous ammonia solution under heating and elevated pressure.

6. A pharmaceutical composition comprising at least one compound of formula (I) according to claim 1 and a pharmaceutically acceptable carrier or excipient.

7. A pharmaceutical composition comprising a compound of formula (I) according to claim 1 in combination with at least one organic nitrate or NO donor.

8. A pharmaceutical composition comprising a compound of formula (I) according to claim 1 in combination with at least one compound which inhibits the breakdown of cyclic guanosine monophosphate (cGMP).

9. A method of treating a cardiovascular disorder comprising administering to a mammal an effective amount of a compound of the formula (I) according to claim 1.

10. A method of treating hypertension comprising administering to a mammal an effective amount of a compound of the formula (I) according to claim 1.

11. A method of treating a thromboembolic disorder or ischaemia comprising administering to a mammal an effective amount of a compound of the formula (I) according to claim 1.

12. A method of treating sexual dysfunction comprising administering to a mammal an effective amount of a compound of the formula (I) according to claim 1.

13. A method of treating an inflammatory disorder comprising administering to a mammal an effective amount of a compound of the formula (I) according to claim 1.

14. A method of treating a central nervous system disorder characterized by a disturbance of the NO/cGMP system, comprising administering to a mammal an effective amount of a compound of the formula (I) according to claim 1.

15. The method of claim 9, 10, 11, 12, 13 or 14, in which said compound of formula (I) is employed in combination with an organic nitrate, an NO donor, or a compound which inhibits the breakdown of cyclic guanosine monophosphate (cGMP).

* * * * *